United States Patent [19]

Hofmann

[11] Patent Number: 5,464,386

[45] Date of Patent: Nov. 7, 1995

[54] TRANSDERMAL DRUG DELIVERY BY ELECTROINCORPORATION OF VESICLES

[75] Inventor: Gunter A. Hofmann, San Diego, Calif.

[73] Assignee: Genetronics, Inc., San Diego, Calif.

[21] Appl. No.: 310,647

[22] Filed: Sep. 22, 1994

Related U.S. Application Data

[63] Continuation-in-part of Ser. No. 219,970, Mar. 30, 1994, which is a continuation-in-part of Ser. No. 931,061, Aug. 17, 1992, Pat. No. 5,318,514.

[51] Int. Cl.⁶ .............................. A61K 9/66; A61N 1/30; A61F 13/00
[52] U.S. Cl. ..................... 604/20; 424/449; 428/402.2
[58] Field of Search ................ 604/19, 20; 607/149, 607/150, 153; 428/402.2; 424/448, 449, 450

[56] References Cited

U.S. PATENT DOCUMENTS

| | | | |
|---|---|---|---|
| 4,921,757 | 5/1990 | Wheatley et al. | 428/402.2 |
| 5,149,539 | 9/1992 | Ledger et al. | 424/449 |
| 5,160,741 | 11/1992 | Cormier et al. | 424/449 |
| 5,312,325 | 5/1994 | Sibalis | 604/20 |

*Primary Examiner*—Lee S. Cohen
*Assistant Examiner*—Stephen Huang
*Attorney, Agent, or Firm*—Baker, Maxham, Jester & Meador

[57] ABSTRACT

A method of transdermal molecular delivery comprises the steps of encapsulating molecules to be delivered in a vesicle, contacting a selected area of a tissue surface with a solution of the vesicles, and applying a pulsed electric field of sufficient amplitude to induce dielectric breakdown of the stratum corneum and to induce transport of the intact vesicle through the pores in the stratum corneum into the underlying tissue to enable diffusion of molecules into the tissue.

20 Claims, 4 Drawing Sheets

TRANSDERMAL DRUG DELIVERY BY ELECTROINCORPORATION OF VESICLES

REFERENCE TO RELATED APPLICATION

The present application is a continuation-in-part of co-pending application Ser. No. 08/219,970, entitled "TRANSSURFACE DRUG DELIVERY BY ELECTROFUSION OF MICROBUBBLES TO THE TISSUE SURFACE", filed Mar. 30, 1994, which is a continuation-in-part of application Ser. No. 07/931,061, entitled "APPLICATOR FOR THE ELECTROPORATION OF DRUGS AND GENES INTO SURFACE CELLS", filed Aug. 17, 1992, now U.S. Pat. No. 5,318,514 dated Jun. 7, 1994.

BACKGROUND OF THE INVENTION

The present invention relates to drug delivery and pertains particularly to a method and apparatus for the transdermal delivery of drugs and other molecules.

The stratum corneum (SC) consists of a thin layer of dead cells with a high electrical resistance. This presents a major obstacle to the administration of drugs, immunizing agents, and genes transdermally. This layer can be perforated by the administration of short electrical field pulses, such as used in electroporation of cells. However, this perforation of the stratum corneum appears more appropriately referred to in terms of dielectric breakdown of the stratum corneum.

In my aforementioned applications, I disclose an apparatus and method for the electroporation of drugs, immunizing agents, and genes into surface cells, and a method and apparatus for the transdermal drug delivery by electrofusion of microbubbles to the tissue surface. In another application Ser. No. 07/907,322, entitled ELECTROPORATION METHOD AND APPARATUS FOR INSERTION OF DRUGS AND GENES INTO ENDOTHELIAL CELLS, filed Jul. 1, 1992, now U.S. Pat. No. 5,304,120 certain methods and apparatus are disclosed for insertion of drugs and genes into endothelial cells. The teachings of these are incorporated herein by reference.

In the second aforementioned parent application, I disclose methods and apparatus for the electroporation of drugs, immunizing agents, and genes into surface cells. In that application, apparatus is disclosed for delivery of a fluid medium carrying preselected molecules to a skin surface and thereafter applying electrical signals by means of electrodes to the surface tissue. The field is applied at a predetermined strength and duration in order to make the walls of the cells of the skin transiently permeable to permit the molecules to enter the preselected cells without damaging them.

One difficulty with the prior apparatus is that the stratum corneum (SC) which consists of a thin layer of dead cells with a high electrical resistance presents a major obstacle to the administration of drugs and genes transdermally. This layer can be perforated by the administration of short electrical field pulses, which creates a dielectric breakdown of the stratum corneum forming pores which can allow the passage of molecules.

Among the prior art relating generally to this field is the Weaver et al U.S. Pat. No. 5,019,034 entitled "Control of Transport of Molecules Across Tissue Using Electro-poration". Weaver seeks an alternative to the traditional syringe and gun injection of medications. He describes a proposal for using high voltage, short duration electrical pulses on the tissue surface to produce electroporation of the tissue to enable drugs and medication to pass into the tissue. However, he does not recognize or address the problem of the obstacle provided by the stratum corneum.

Another patent of interest is that of Grasso U.S. Pat. No. 4,955,378 entitled "Apparatus and Methods for Performing Electrofusion at Specific Anatomical Sites". He discloses a method of fusing biological particles to living tissue, preferably on corneas and in cervical areas. The tissue consists of living cells which are able to completely fuse with the biological particles, or live cells. Again, this does not address or solve the problem of transdermal transport of drugs, immunizing agents, and genes presented by the resistance of the stratum corneum. Also, neither of these patents provide or suggest any means to force the drugs, immunizing agents, or genes into or across the tissue surface.

The co-pending parent application presents an invention to overcome the problems of the prior art by providing means to overcome the resistance to the administration of drugs transdermally presented by the stratum corneum. In accordance with that invention, drugs, immunizing agents, or genes are loaded into microbubbles, the microbubbles are brought into physical contact with the tissue surface and a pulsed electrical field is applied between the microbubbles and the tissue by means of electrodes. This forms pores at the interface of the microbubbles and the tissue, such that the microbubbles fuse with the tissue and form a channel through which drugs and genes, which are under pressure from the microbubble to enter through the tissue. It is also applicable to the transport of drugs, immunizing agents, and genes across surfaces of other tissue such as membranes.

One problem with this approach is that it fails to provide sufficient control over the diffusion of drugs or the like in or into the tissue.

It is desirable that improved methods and apparatus be available for the transdermal delivery of drugs, immunizing agents, and genes.

SUMMARY AND OBJECTS OF THE INVENTION

It is the primary object of the present invention to provide an improved method and apparatus for transdermal drug delivery by electroincorporation of vesicles.

In accordance with the primary aspect of the present invention, drugs or genes are loaded into vesicles, the vesicles are brought into physical contact with the tissue surface and a pulsed electrical field is applied between the vesicles and the tissue by means of electrodes. This forms pores in the stratum corneum (SC), such that the vesicles which carry drugs, immunizing agents, and genes, enter through the SC into the tissue.

BRIEF DESCRIPTION OF THE DRAWINGS

The above and other objects and advantages of the present invention will be appreciated from the following specification when read in conjunction with the accompanying drawings wherein.

DETAILED DESCRIPTION OF THE PREFERRED EMBODIMENTS

The present invention takes advantage of dielectric breakdown of the stratum corneum (SC) to transfer vesicles containing drugs and genes across the SC surface into the underlying tissue and possibly into the blood stream. When desirable, subsequent electroporation may be applied to improve the uptake of drugs, genes, DNA or the like, into cells in the living tissue of humans and other living organism. Various techniques including electroporation is used to load molecules such as drugs and DNA into vesicles of a size up to several μm diameters. The vesicles are then applied to the SC and electrodes are then applied over the vesicles. Electrical field pulses are then used to create dielectric breakdown of the stratum corneum or other tissue surface forming passages through which the vesicles and the drugs or other molecules pass into the underlying tissue. The vesicles are then broken down and the molecules diffused into the tissue.

Electroporation involves the transient formation of pores in tissue or cell membranes utilizing a short pulse of high-voltage electric fields. Once these pores are formed in the cell membranes, DNA and other molecules can enter the cells through these pores in the cell walls. Thereafter, they stay encapsulated in the cell and the cell walls reseal themselves. The DNA or other gene or drug can then act within the cell to alter the cell properties.

Figure 1:
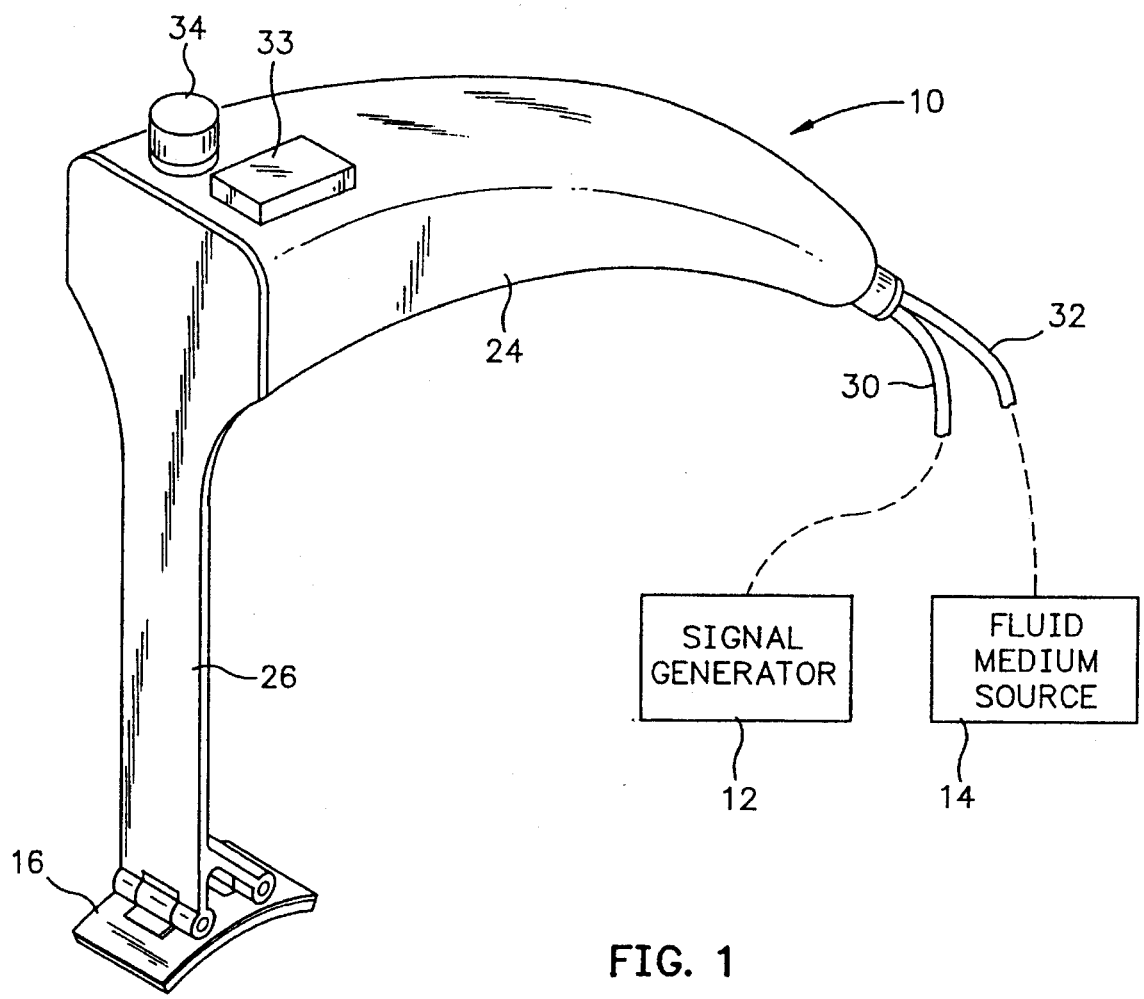
FIG. 1 is a perspective view of an apparatus for carrying out the process of the present invention.
Figure 2:
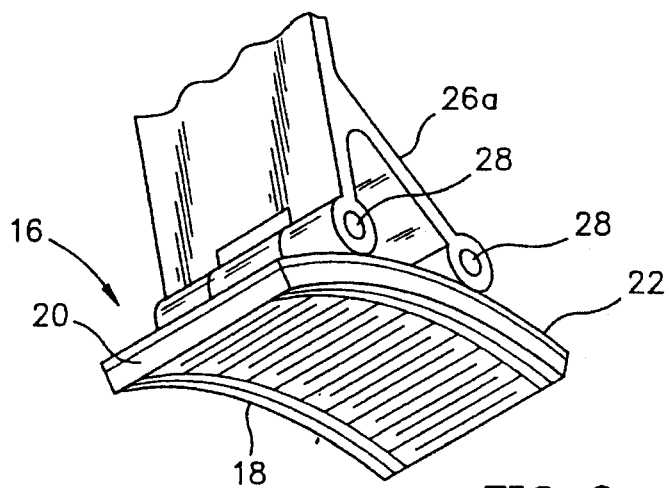
FIG. 2 is an enlarged view of the head assembly of the FIG. 1 embodiment.

Referring to FIG. 1, an exemplary embodiment of an apparatus which may be utilized in carrying out the process of the present invention, is illustrated. The device comprises a manually positionable applicator designated generally by the numeral 10 which is connected to a signal generator 12 and a fluid medium source 14. The applicator 10 has a head assembly 16 which engages and applies vesicles with genes, immunizing agents or drugs; and electrical pulses to a preselected surface tissue region of a patient. Details of the head assembly are illustrated in FIG. 2.

The head assembly comprises an electrode array 18 which is carried or mounted on a carrier or applicator such as an open pore foam elastomer 20 carried by flexible semirigid or firm dielectric planar support member 22. Adjacent parallel segments of the conductors serve as electrodes for application of the electric field to the tissue surface. The electrodes are preferably small and closely spaced, such as about 0.2 mm width at about 0.2 mm spacing. The applicator may also be a small patch with electrodes on a surface thereof.

The applicator 10 (FIG. 1 ) further includes a handle portion 24 and an arm portion 26 on which is mounted the head assembly 16. The head assembly 16 is connected to a Y-shaped distal end 26a by means of a pair of pins 28. These pins enable the head to flex and conform to the curvature of the skin surface.

The terminal ends of the conductor 18 are connected to the signal generator 12 by way of an electrical cable 30. A fluid medium carrying vesicles containing the molecules or drugs is contained within the fluid medium source 14, which may include a suitable motorized pump or pressure source, not shown. The fluid medium source 14 is coupled to the elastomer foam 20 by flexible tube 32 which extends to the applicator 10 to the foam applicator. An actuator button 34 on the handle 24 of the applicator may be depressed to activate a valve (not shown) and deliver a suitable quantity of the fluid medium to the foam elastomer 20. The elastomer 20 provides a sponge-like substrate for holding a predetermined quantity of the fluid medium. The applicator and signal generator functions as more fully described in the aforementioned parent application, now allowed, which is incorporated herein by reference as though it were fully set forth. A button 33 is depressed to activate the signal generator.

The invention can also be carried out by a catheter type apparatus and methods disclosed in the aforementioned Ser. No. 07/907,322 which is incorporated herein by reference as though fully set forth. This provides a more convenient apparatus for the delivery of drugs and genes across tissue surfaces and membranes such as in body cavities. The present invention was devised to overcome the problem presented by the stratum corneum. However, it is applicable to the insertion of molecules such as drugs and genes across other tissue surfaces in body cavities and open wounds. Certain modifications may be necessary to the illustrated apparatus for these other applications.

Figure 3:
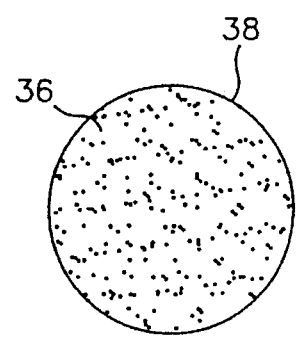
FIG. 3 is a diagrammatic illustration of a vesicle loaded with molecules of drugs, immunizing agents or genes.

Referring to FIG. 3, the process of the present invention is carried out by first encapsulating the drugs or genes 36 which are to be delivered transdermally into vesicles 38 such as microbubbles as carriers. These vesicles can be liposomes, erythrocyte ghosts or other vesicles. The vesicles may also be of a matrix design where the drug or other molecules are encapsulated within the matrix. This would enable the provision of a time release function. The encapsulation of the molecules can be carried out by any one of a number of known processes, including electroporation.

Figure 4:
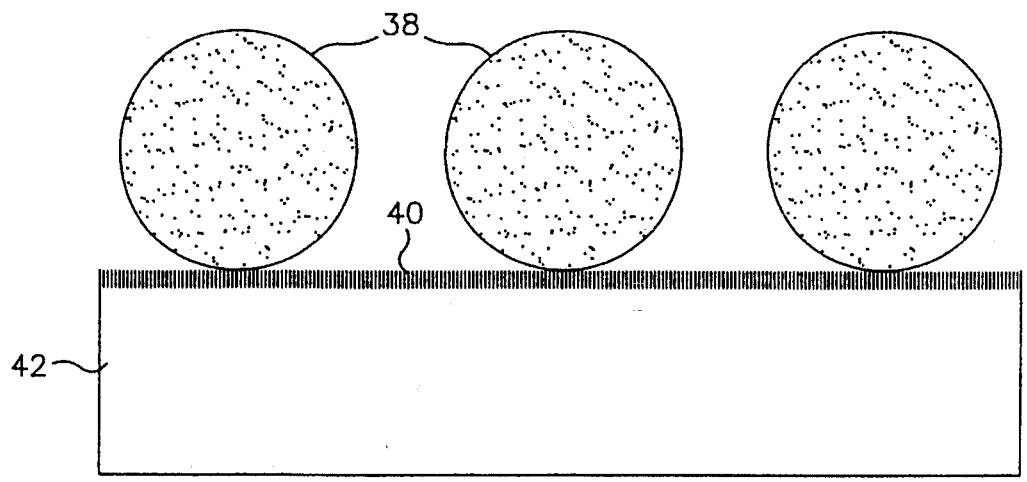
FIG. 4 is a diagrammatic illustration of multiple vesicles applied to the surface of the stratum corneum.

The loaded vesicles 38, as illustrated in FIG. 4, are then brought into contact with the tissue surface or stratum corneum 40 of a skin layer 42 by suitable means and are positioned between pairs of closely spaced electrodes 44 and 46. This can be carried out by the apparatus of FIG. 1, wherein a fluid carry the vesicles and applied by the sponge 20 would be positioned between the electrodes 18 on the surface of the applicator.

Figure 5:
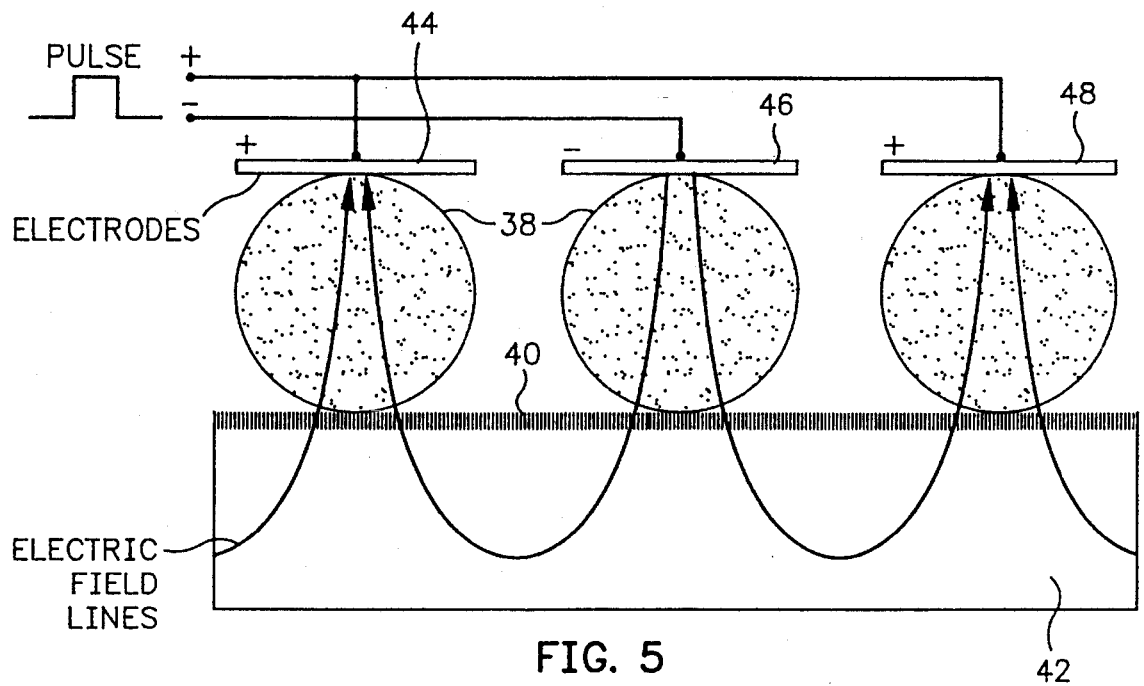
FIG. 5 is a diagrammatic illustration of a third step of applying electrodes and a pulse electrical field between the microbubbles and skin or stratum corneum.

Thereafter, a short voltage pulse is applied between the electrodes so that the electric fields of sufficient amplitude are generated to induce dielectric breakdown forming pores in the stratum corneum and induce the vesicle to pass through the pores into the underlying tissues. As shown in FIG. 5, the electric field is applied so that useful electric field lines are perpendicular to the tissue surface or stratum corneum surface. Typical electrical parameters for the stratum corneum are a field strength of 20 to about 60 kV/cm, which can be generated with moderate voltages of 20 to 120 volts with a pulse length of 10 microseconds (μsec) to 10 milliseconds (msec). This electric field induces a dielectric breakdown and pores in the stratum corneum and the vesicles or microbubbles pass through the pores in the SC. Other tissue surfaces will typically require less field strength.

Figure 6:
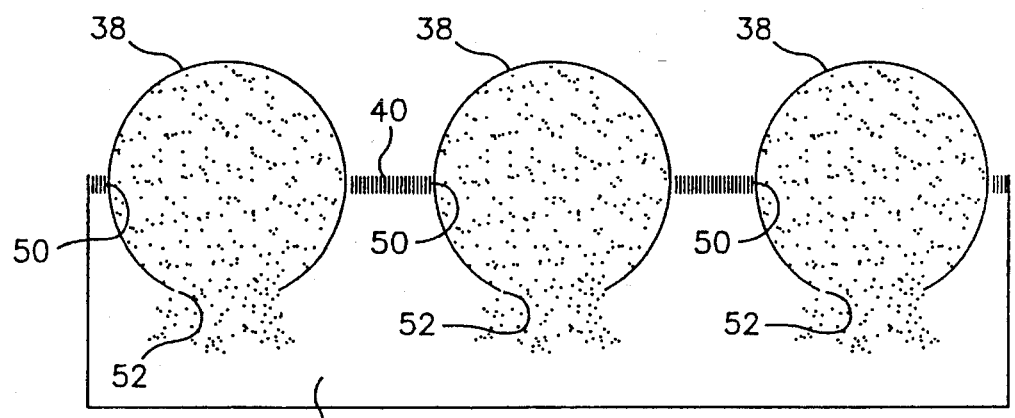
FIG. 6 is a diagrammatic illustration of the formation of pores and the passage of vesicles or microbubbles through the pores in the stratum corneum.
Figure 7:
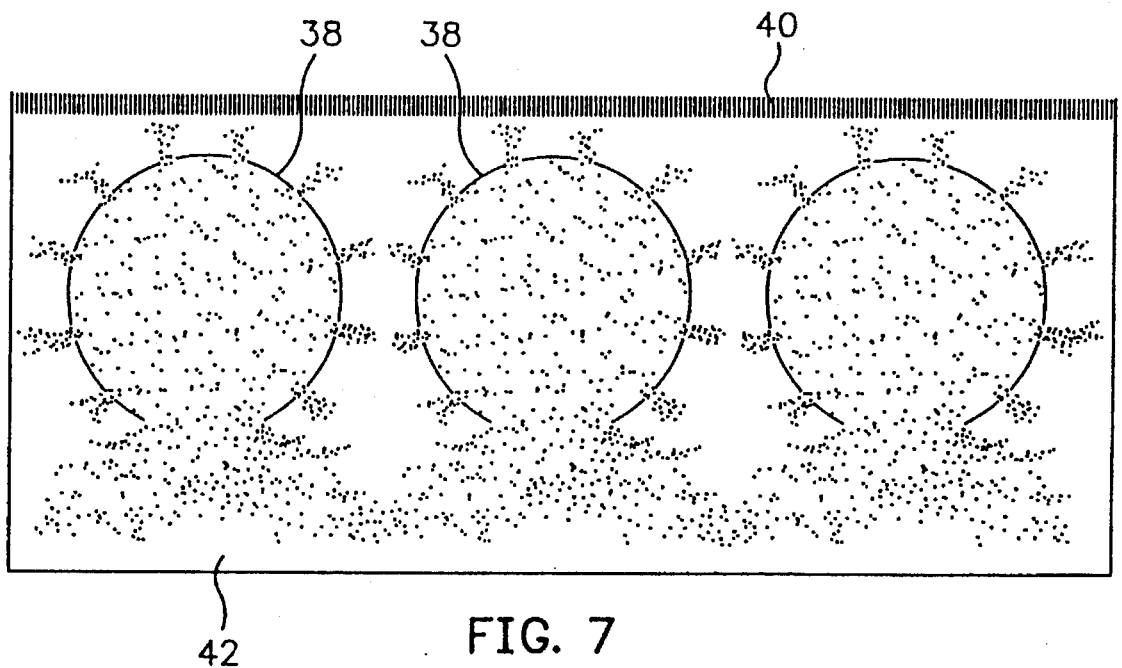
FIG. 7 is a diagrammatic illustration of the vesicles below the stratum corneum and the passage of drugs, immunizing agents or genes from the vesicles into the skin below the stratum corneum.

The dielectric breakdown in the stratum corneum allow the vesicles to pass through open pores 50 as illustrated in FIG. 6. These pores open up and allow the vesicles to pass through and into the dermis underlying the stratum corneum as illustrated in FIG. 7. Enzymes within the dermis act to break down walls of the vesicles forming openings 52 and cause them to release the molecules into the dermis. Since the stratum corneum consists essentially of dead material, the channel will not close as quickly as it would in a live tissue. This allows the vesicles containing drugs or genes to pass through the surface layer into the underlying skin tissue.

Other forms of a delivery system could be utilized, such as a small system strapped to the arm or other body part or momentarily connected, containing a rechargeable battery-powered pulse power supply with a reservoir containing vesicles in suspension with the drug encapsulated. The applicator would have the basic components as the device in FIG. 1 such that by pushing one button, a preselected amount of vesicles is delivered to the skin between the electrodes. The vesicles are pressed against the skin for good mechanical contact. Activating another button or switch delivers an electrical pulse to the electrodes which delivers the vesicles through the stratum corneum.

A special patch can also be applied to the tissue surface. The vesicles can be contained in the patch which also contains the electrode structure to create the electric field. The electrode structure can be similar to FIG. 2 and inside or on a surface of the patch. The electrode structure is connected to two electrodes outside the patch so that a pulse generator can be connected momentarily to these outside electrodes to provide a voltage pulse. The patch is preferably provided with an adhesive border to adhere it to the skin or tissue. It is also preferably provided with a protective cover which can be peeled off before adhering the patch to the skin or tissue.

If the drug is to be transported into the cells, a second pulse after allowing appropriate diffusion time, is applied to open up pores in the cells. This allows the cells to take up the drug or molecules by electroporation.

A drug delivery time profile can be created by mixing different size vesicles. The flux can then be controlled by the pore size and the number of vesicles delivered. The process of the present invention could also be combined with iontophoresis as an additional driving force. The iontophoresis takes advantage of ion charges to cause a migration of the ions or molecules through existing passages or pores in the tissue. The combination could use electroincorporation to deliver vesicles through the SC and then use iontophoresis to induce migration of the drugs, immunizing agents, or genes further into selected tissue.

The present invention has been demonstrated in experiments as follows:

1. Labelled calcein was loaded into small liposomes of about 300 nm in diameter, as well as large liposomes of 9 μm diameter. These were placed on the skin of hairless mice and electrodes placed on top of the liposomes in order to create electric fields with components perpendicular to the skin. A pulse of about 60 V and 1.2 msec pulse length was applied.

2. Examination by fluorescent microscopy disclosed that calcium was present in the epidermis and dermis after the pulse, not just in the hair follicles but also in between. Further examination by transmission electromicroscopy "TEM" revealed that whole liposomes were present after the pulse below the SC. This indicates that the liposomes which average in size about 300 nm or 9 μm had crossed the stratum corneum during the pulse.

3. Further study and examination through TEM disclosed that liposomes decomposed and released their contents into the tissue in the dermis. Further tests showed that calcein was entering the blood stream within minutes after the pulse. Further analysis revealed that starting with an amount of calcein on the skin of 25 μg the amount found in the blood was about 300 ng per ml. Assuming a total amount of blood of about 5 ml, the total amount of calcein in the blood was about 1.5 μg. This calculates to an efficiency of 1.5 per 25 which equals about 6%.

In plotting this over a period of time, the plot revealed that the concentration of calcein in the blood rose dramatically during the first five minutes, peaking at 15 minutes and dropping off gradually along an almost constant slope at 90 minutes.

Figure 8:
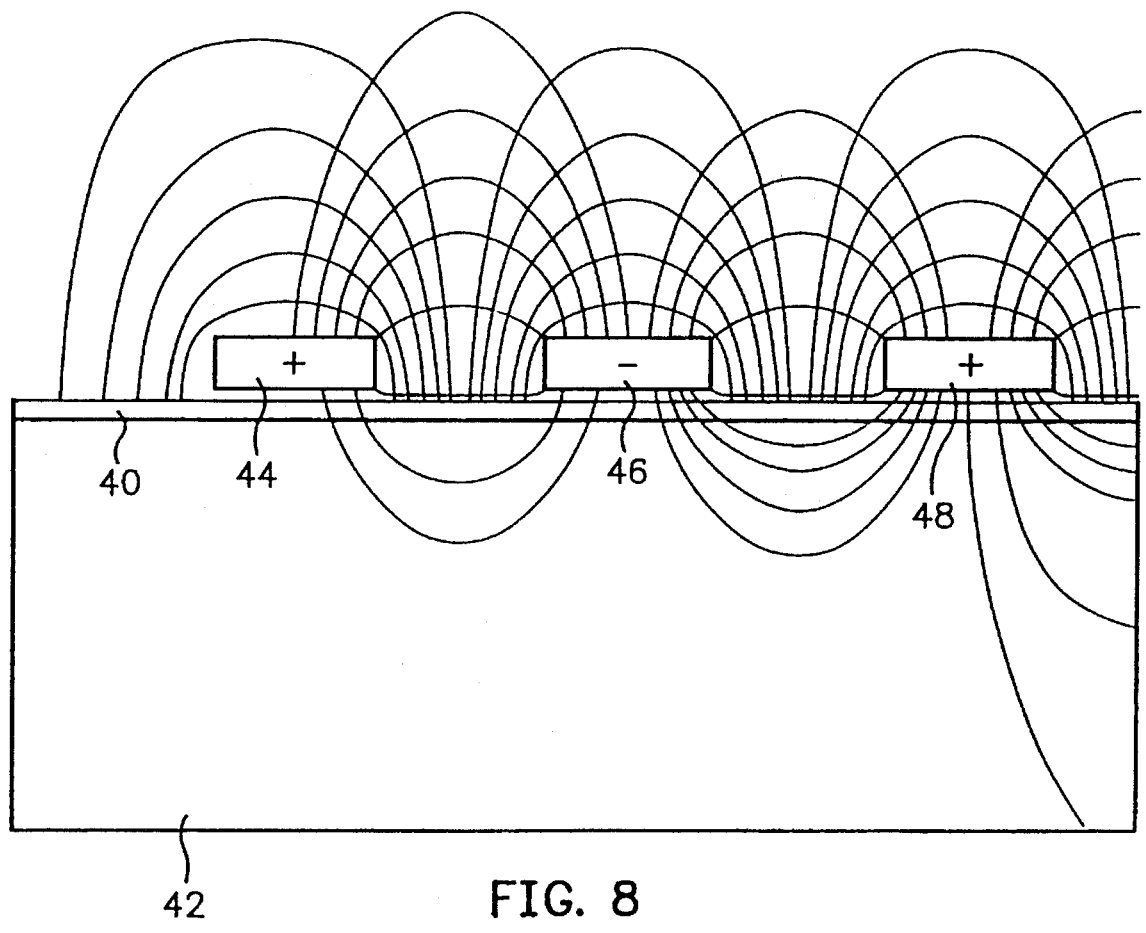
FIG. 8 is a diagrammatic illustration of a equipotential and field line distribution around electrodes on the surface of the stratum corneum.

Referring to FIG. 8, an equal potential and electric field line distribution around electrodes of about 0.2 mm in width spaced about 0.2 mm. The stratum corneum is intact with a high resistivity. The equal potential lines are concentrated in the stratum corneum, leading to a high field strength. The stratum corneum shields the underlying epidermis from the field.

Figure 9:
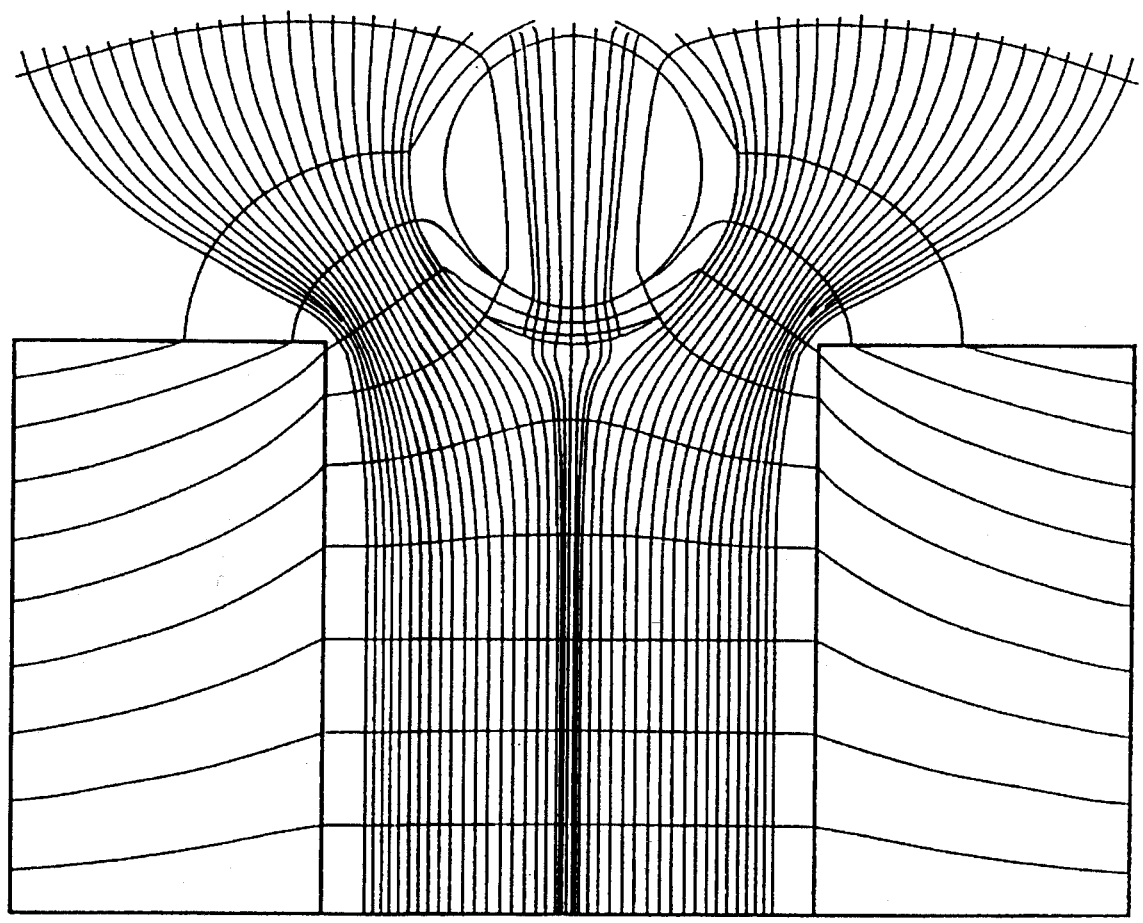
FIG. 9 is a diagrammatic illustration of the field lies around a liposome and through a pore in the stratum corneum.
Figure 10:
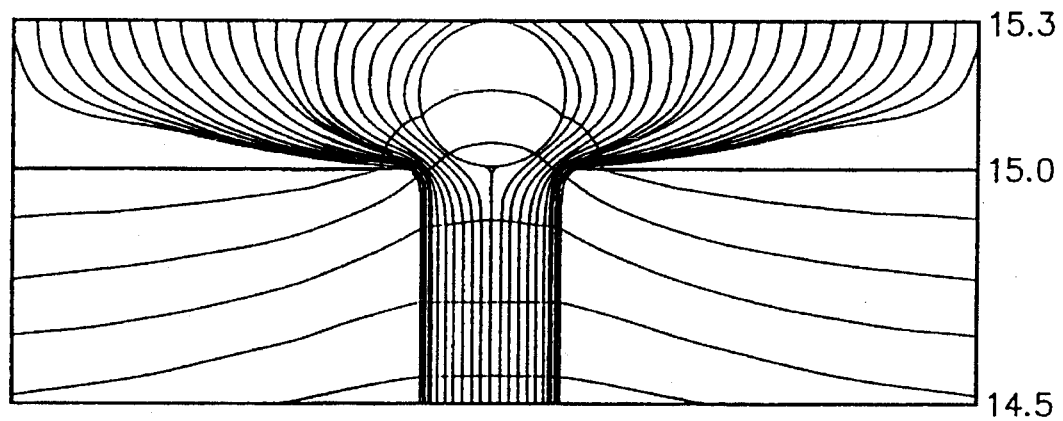
FIG. 10 is a diagrammatic illustration like FIG. 9 of a solid particle.

Referring to FIG. 9 a field plot around a liposome of about 300 μm in diameter in a hole in the SC is shown. Charged liposomes will experience a Coulomb force (force on charged particles by an electric field) and can be drawn into the SC and epidermis after break-down of the SC. Uncharged liposomes, such as small liposomes used in my experiments, do not experience a Coulomb force in a homogenous electric field. They are polarized in the electric field and a subjected to a force caused by the inhomogeneous field in the pores of the SC. This "dielectrophoretic" force is proportional to the product of the field strength and the gradient of the field. This field distribution around a liposome and solid particle in proximity to a pore in the SC is illustrated respectively in FIGS. 8 and 9.

The following simple model describes the uncharged liposome movement through a pore driving by the electrophoretic force:

1. Dielectric breakdown of $SC$: $E \geq 20$ kV/cm

2. Dielectrophoretic force $F_D$ on neutral particles:

$$F_D = \frac{aV}{2} \nabla |E|^2$$

$a$ = Polarizability
$V$ = Volume
$E$ = Field Strength

3. Stokes force $F_S$ determines velocity $v$:

$$F_S = 6\pi r v \eta$$

$$v = \frac{a}{9\eta} r^2 \nabla |E|^2$$

$r$ = radius of particle
$v$ = velocity
$\eta$ = viscosity of medium

4. Pulse duration determines penetration depth $d$:

$$d = VTN$$

$T$ = pulse length
$N$ = number of pulses

-continued

5. Example: $2r = 9$ um $E = 36$ kV/cm 3 pulses at 1 msec each

Penetration depth $d = 129$ um

A more accurate estimate would require knowledge of the shape of the electric field in pores in the SC. Electroincorporation is expected to work well with solid vesicles as well as with vesicles with a membrane.

Dielectrophoresis as well as electrophoresis as a driving force through the SC do not require a vesicle with a membrane. This is different from the electrofusion mechanism where a membrane is essential. It is expected that electroincorporation can be applied to a wide variety of vesicles or microspheres which contain drugs in a matrix. It will be appreciated that the vesicles must be small enough to pass through pores or openings formed in the SC and skin. At the present time I believe this to be about 9 μm or slightly larger.

The following study has been conducted:

| | |
|---|---|
| Chemical Delivered | Calcein (MW 623) |
| Animal Model | Shaved Mouse |
| Analysis | Fluorescence Microscopy |
| | Picture shows tissue to a depth of about 1,500 μm |
| | Stratum Corneum at the top. |

Experimental Conditions:

1. Topical Calcein
2. Topical Calcein plus electroporation
3. Liposome calcein (24 hours incubation)
4. Liposomal calcein plus electrofusion (5 minutes incubation after electroporation)

Conclusions:

1. Little, if any, penetration
2. Minor penetration near surface
3. Major penetration into hair shafts, no uptake into the blood
4. Major penetration into tissue between hair shafts, detectable in the blood in less than 15 minutes.

The results of this limited experiment showed that the best penetration of the skin into the underlying skin or tissue was seen in Example 4, with the liposome-encapsulated calcein and electric pulses.

I have illustrated and described my invention by means of specific embodiments, it is to be understood that numerous changes and modifications may be made therein without departing from the spirit and scope of the invention as defined in the appended claims.

I claim:

1. A method of molecular delivery through a surface tissue, comprising the steps of:

selecting a quantity of molecules to be delivered through the surface tissue;

selecting a quantity of vesicles as carriers;

encapsulating said molecules in said vesicles;

contacting a selected surface area of the surface tissue with a quantity of said vesicles; and applying a pulsed electric field of sufficient amplitude and duration to induce pores in the surface tissue and to induce transport of said vesicles through said pores into a underlying tissue to enable diffusion of said molecules into the tissue.

2. A method according to claim 1 wherein said surface tissue is a stratum corneum and said electric field has a strength of from about 10 to about 60 kV/cm with a pulse length of from 10 usec to 10 msec.

3. A method according to claim 1 wherein selecting said vesicles to have a membrane and encapsulating the molecules within the membrane.

4. A method according to claim 1 wherein selecting said vesicles to be of a matrix construction and encapsulating the molecules within the matrix.

5. A method according to claim 1 wherein selecting said vesicles to have an electrical charge.

6. A method according to claim 1 wherein selecting said vesicles to be neutral.

7. A method according to claim 1 therein the step of applying the electric field includes applying a plurality of closely spaced electrodes to a surface area of a stratum corneum and applying pulses of from 10 to several hundred volts with a pulse length of between 100 usec to 100 msec.

8. A method according to claim 7 wherein selecting said vesicles to have a membrane and encapsulating the molecules within the membrane.

9. A method according to claim 8 wherein selecting said vesicles to have an electrical charge.

10. A method according to claim 8 wherein selecting said vesicles to be neutral.

11. A method according to claim 7 wherein selecting said vesicles to be of a matrix construction and encapsulating the molecules within the matrix.

12. A method according to claim 11 wherein selecting said vesicles to have an electrical charge.

13. A method according to claim 11 wherein selecting said vesicles to be neutral.

14. A method of transdermal delivery of molecules, comprising the steps of:

encapsulating molecules to be delivered in a vesicle;

contacting a selected area of stratum corneum surface with a quantity of the encapsulated molecules; and applying a pulsed electric field of sufficient amplitude from about five volts to about six hundred volts and sufficient duration of from about one hundred usec to about one hundred msec to create open pores in said area of stratum corneum of sufficient size to receive vesicles and to induce passage of said vesicles through said stratum corneum into underlying tissue.

15. A method according to claim 14 wherein selecting said vesicles to have a membrane and encapsulating the molecules in the membrane.

16. A method according to claim 14 wherein forming said vesicles in the form of a matrix and encapsulating the molecules within the matrix.

17. A method of transdermal delivery of molecules, comprising the steps of:

encapsulating molecules to be delivered in a matrix of a vesicle, wherein the vesicles are constructed to have a time release characteristic;

contacting a selected area of stratum corneum surface with a quantity of the encapsulated molecules; and applying a pulsed electric field of sufficient amplitude from about five volts to about six hundred volts and sufficient duration of from about one hundred usec to about one hundred msec to create open pores in the area of stratum corneum of sufficient size to receive the vesicles and to induce passage of the vesicles through the stratum corneum into the tissue.

18. A method according to claim 17 wherein selecting said vesicles to have an electrical charge.

19. A method according to claim 17 wherein selecting said vesicles to have no electrical charge.

20. A method according to claim 15 wherein selecting said vesicles to be neutral.

* * * * *